(12) United States Patent
Grenfell et al.

(10) Patent No.: US 6,416,323 B1
(45) Date of Patent: Jul. 9, 2002

(54) ASPIRATING DENTAL SYRINGE WITH NEEDLE SHIELD

(75) Inventors: William W. Grenfell, Baldwin; Ronald R. Klawitter, Berger, both of MO (US)

(73) Assignee: Safety Syringes, Inc., Carlsbad, CA (US)

( * ) Notice: Subject to any disclaimer, the term of this patent is extended or adjusted under 35 U.S.C. 154(b) by 0 days.

(21) Appl. No.: 09/569,692

(22) Filed: May 11, 2000

(51) Int. Cl.$^7$ ................................................ A61C 5/04
(52) U.S. Cl. ...................... 433/90; 604/195; 604/198
(58) Field of Search ................................ 604/110, 198, 604/192, 187, 263, 195; 433/90, 89

(56) References Cited

U.S. PATENT DOCUMENTS

| | | |
|---|---|---|
| 2,571,653 A | 10/1951 | Bastien |
| 3,583,399 A | 6/1971 | Ritsky |
| 4,333,456 A | 6/1982 | Webb |
| 4,333,457 A | 6/1982 | Margulies |
| 4,381,779 A | 5/1983 | Margulies |
| 4,655,751 A | 4/1987 | Harbaugh |
| 4,898,590 A | 2/1990 | Andors |
| 4,911,693 A | 3/1990 | Paris |
| 4,923,445 A * | 5/1990 | Ryan ............................ 604/195 |
| 5,045,066 A | 9/1991 | Scheuble et al. |
| 5,057,087 A | 10/1991 | Harmon |
| 5,059,184 A | 10/1991 | Dyke |
| 5,147,326 A | 9/1992 | Talonn et al. |
| 5,207,646 A | 5/1993 | Brunel |
| 5,215,535 A | 6/1993 | Gettig et al. |
| 5,407,431 A * | 4/1995 | Botich et al. ................ 604/110 |
| 5,492,536 A * | 2/1996 | Mascia ........................ 604/197 |
| 5,531,706 A | 7/1996 | de la Fuente |
| 5,554,122 A | 9/1996 | Emanuel |
| 5,624,400 A | 4/1997 | Firth et al. |
| 6,086,568 A * | 7/2000 | Caizza ......................... 604/218 |

OTHER PUBLICATIONS

PCT Publication No. WO 99/16489, Lockable Safety Shield Assembly for a Prefillable Syringe, H. Jansen, et al., Apr. 8, 1999.

* cited by examiner

Primary Examiner—Nicholas D. Lucchesi
(74) Attorney, Agent, or Firm—Lyon & Lyon LLP

(57) ABSTRACT

A self-shielding aspirating dental syringe includes a body having proximal and distal ends and a cavity therein for receiving a medicine cartridge. The distal end has a double-ended needle attached thereto, and the proximal end has an opening for inserting the cartridge into the cavity, and to which a plunger assembly may be attached. A shield is slidable on the body between retracted and extended positions for uncovering and covering the needle, respectively. Cooperating detents and detent pockets are molded on the shield and body for securing the shield in the extended position. A lever is molded on the shield that is pivotable for directing the detents radially outwardly to disengage the detents from the distal detent pockets and allow retraction of the shield from the extended position. A latch is molded on the shield for locking the lever and preventing subsequent retraction of the shield from the extended position.

33 Claims, 12 Drawing Sheets

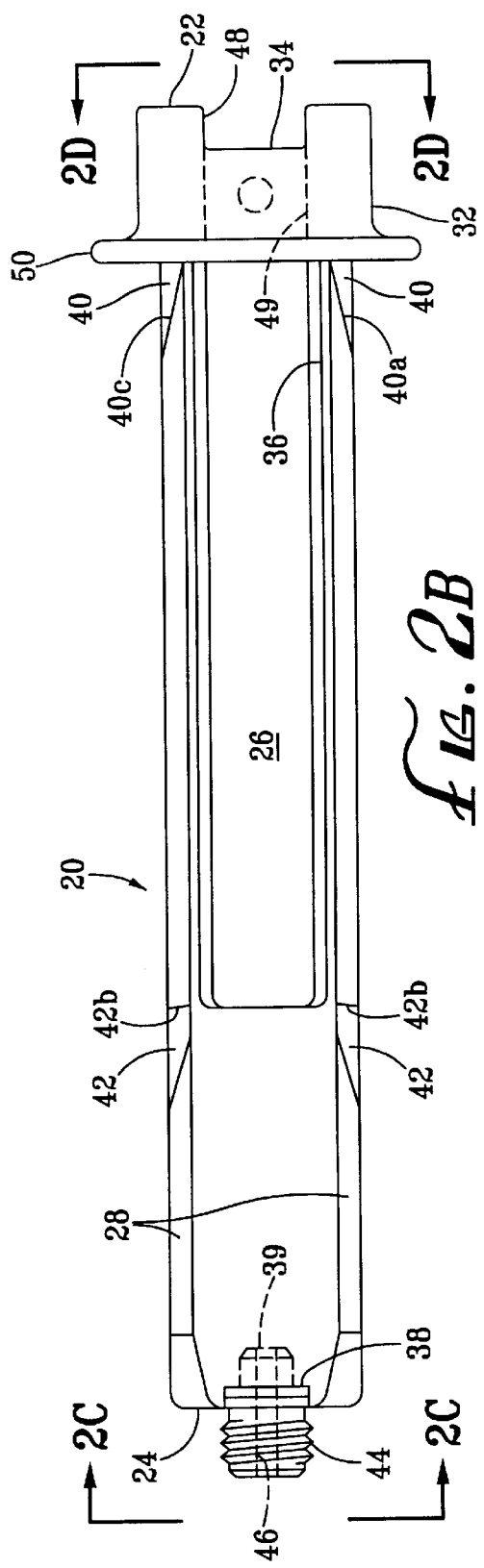
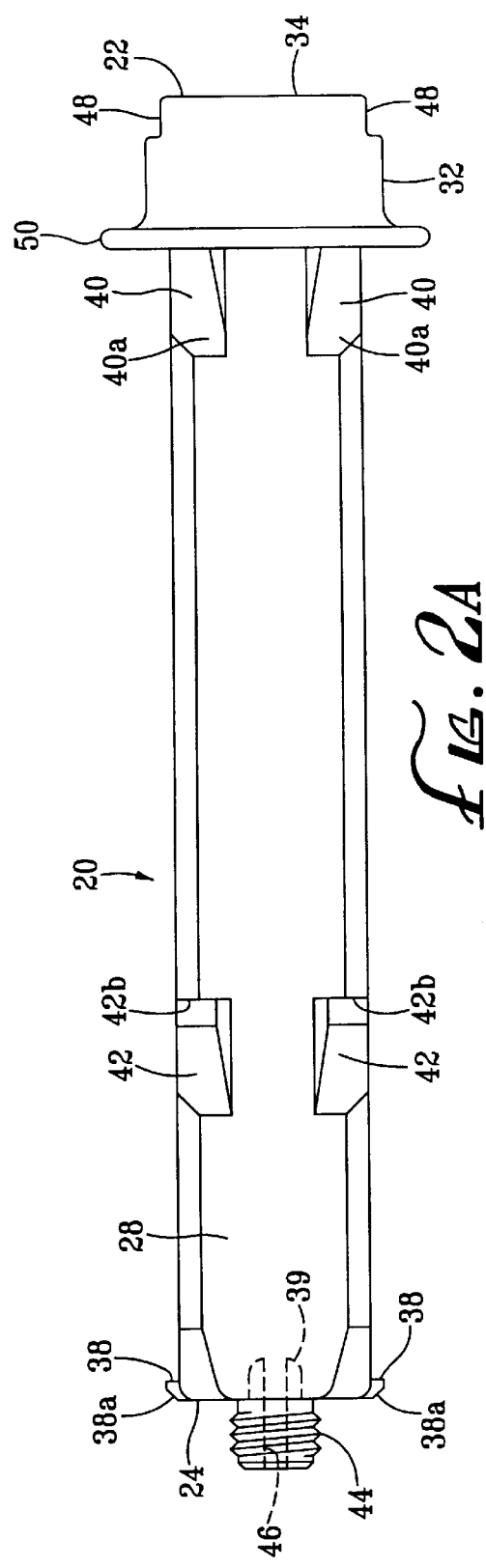

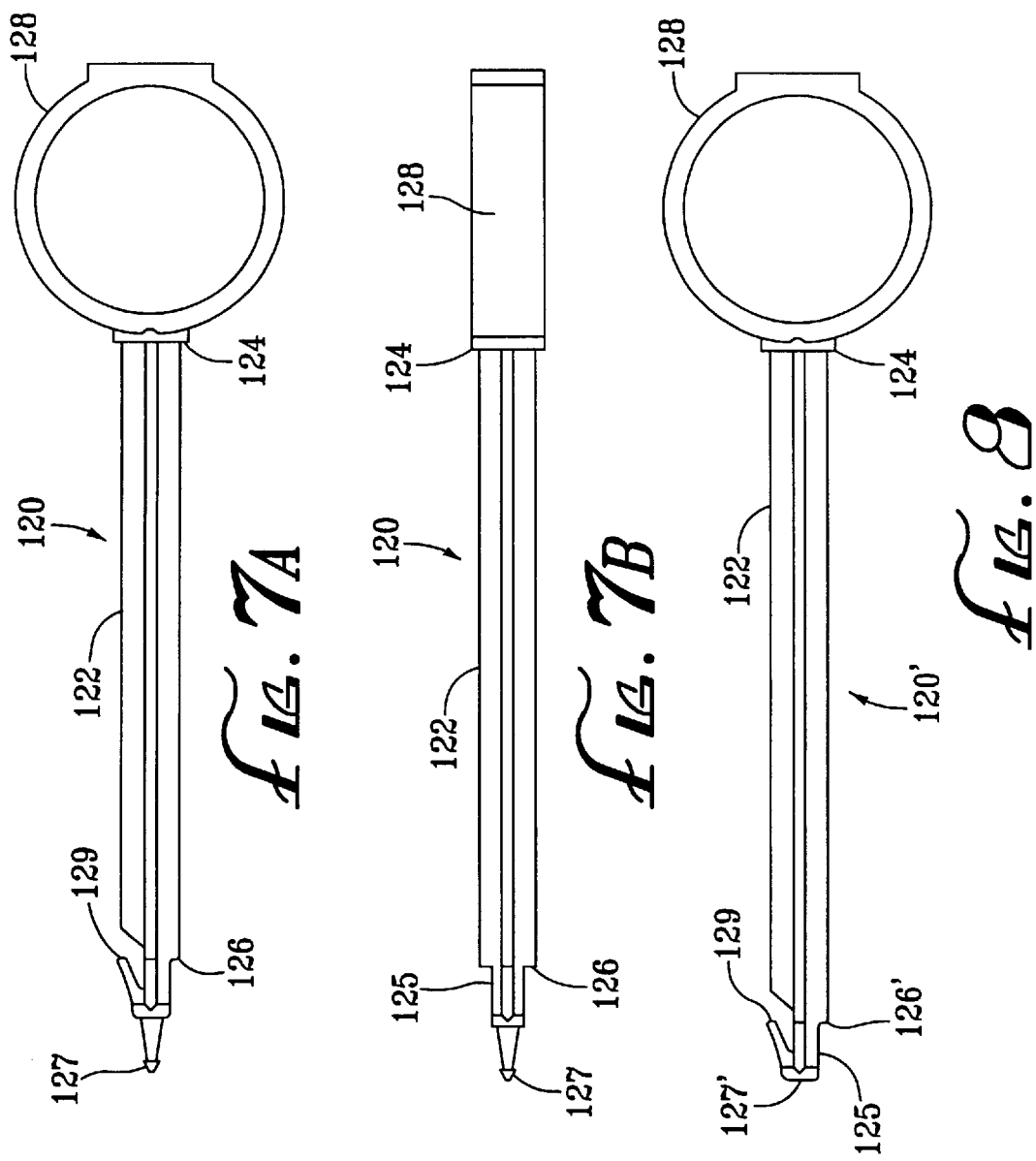

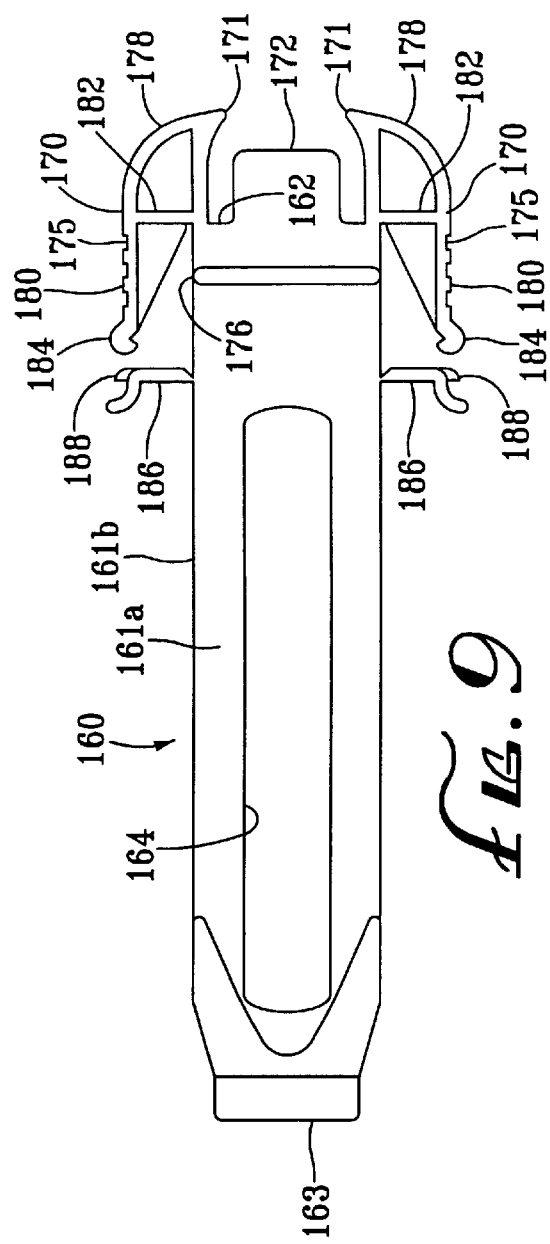
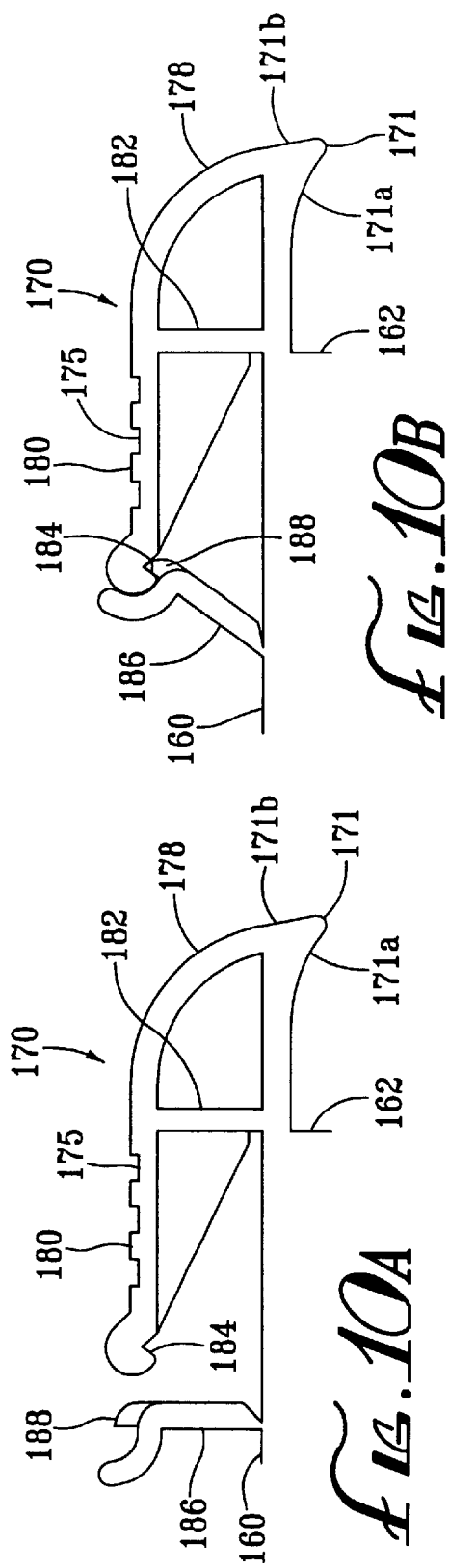
Fig. 9
Fig. 10B
Fig. 10A

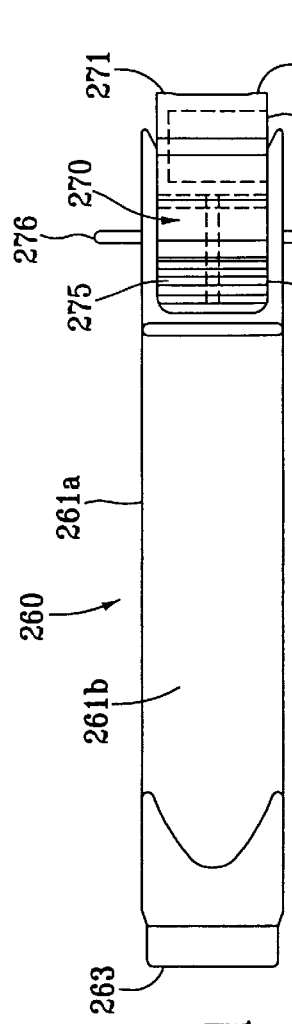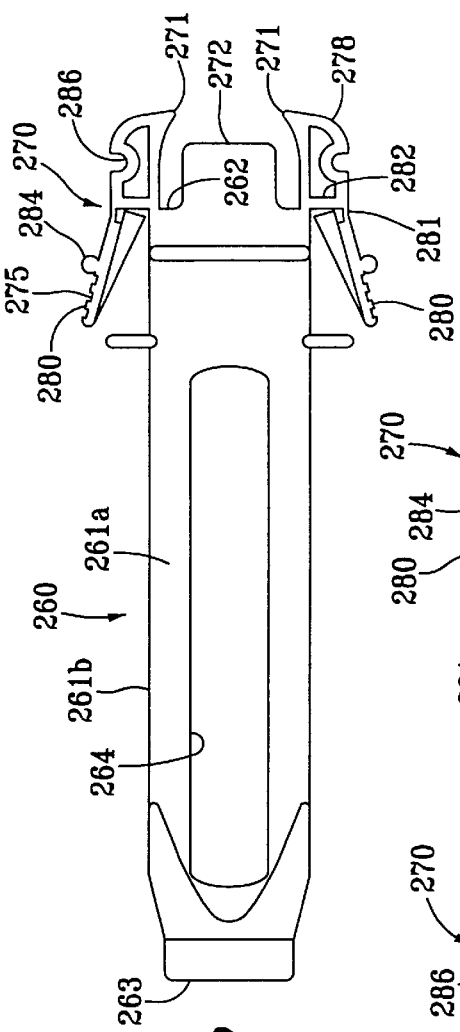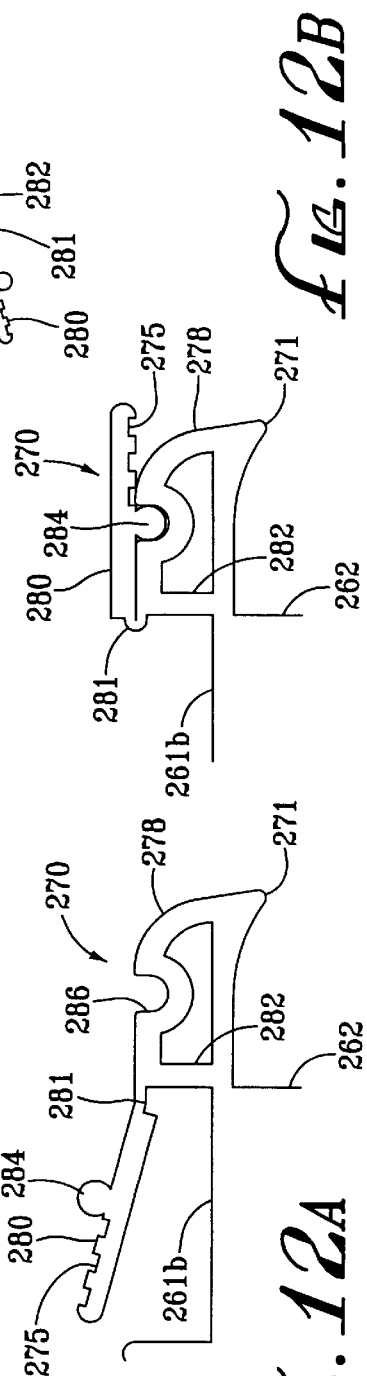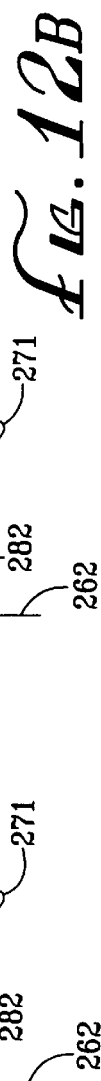

ASPIRATING DENTAL SYRINGE WITH NEEDLE SHIELD

FIELD OF THE INVENTION

The present invention relates generally to safety systems for syringes, and more particularly to a dental syringe for a medical cartridge that includes a shield for selectively covering the needle of the syringe after medication is dispensed from it.

BACKGROUND

Medication is often dispensed using a medical cartridge, such as an ampoule or syringe, received in a syringe holder or adapter. The cartridge generally includes a barrel having a piston in one end and a penetrable seal or rubber stopper on the other end. The syringe adapter generally is a hollow body having a cavity for receiving the cartridge therein. The body may have an open end allowing axial loading of a cartridge into the cavity, or it may include an opening for side loading.

A double-ended needle may be provided on one end of the body for penetrating the seal on the cartridge received in the cavity to allow delivery of medication in the cartridge through the needle into a patient. A plunger assembly may be provided on the other end of the body for engaging and moving the piston in the cartridge to deliver medication and/or to aspirate the cartridge. Alternatively, the cartridge itself may include a needle instead of a penetrable seal, and the body may simply have a hole through which the needle may be directed when the cartridge is received in the cavity.

Because of the threat of communicable diseases, a number of syringes and adapters have been proposed to prevent accidental needle sticks or inadvertent reuse of needle devices. Many of these devices, however, are not easy to use or are complicated to manufacture, resulting in less effective disposable syringe devices. For example, retractable needle devices have been proposed that allow the needle of the syringe to be withdrawn into the barrel of the syringe after medication is dispensed from it. Such devices, however, generally require customized cartridges and cannot accommodate conventional cartridges.

Extendable shield devices have also been proposed that include a slidable shield mounted on a body for receiving a cartridge. The shield may be directable between a retracted position exposing the needle for use, and an extended position substantially covering the needle for disposal. Some devices allow the shield to freely slide back and forth between the retracted and extended positions. Such devices, however, may result in a shield that may inadvertently advance towards the extended position during use, possibly interfering with an injection, or that may expose the needle after use, risking an accidental needle stick.

To protect against this, the shield and body may include cooperating elements, such as detents and detent pockets, that automatically lock the shield when advanced to the extended position. Thus, the shield may be substantially permanently locked, covering the needle to facilitate safe disposal. These cooperating elements may work well for a single use device, but if multiple injections need to be given to a patient, it may be desirable to selectively cover the needle between injections, but eventually lock the shield in the extended position for final disposal.

Accordingly, it is believed that a syringe adapter that allows selective extension or retraction of a needle shield would be considered useful.

SUMMARY OF THE INVENTION

The present invention is directed to self-shielding syringes, such as an aspirating dental syringe, and to methods of using such a syringe. In one embodiment, the syringe includes a body having proximal and distal ends and a cavity therein for receiving a medicine cartridge, the distal end having an opening through which a needle may extend. A shield is slidably attached to the body that is slidable between a retracted position wherein a needle extending from the distal end of the body is exposed through a distal end of the shield, and an extended position wherein the needle is substantially covered by the shield. A cooperating detent and detent pocket is provided on the shield and body for releasably holding the shield in the extended position. A latch is also provided for locking the detent in the detent pocket for preventing subsequent retraction of the shield from the extended position.

A needle may extend from the distal end of the body. The needle may be molded directly into the distal end of the body, or may include a threaded hub for attaching the needle to a mating threaded hub on the body. More preferably, the needle includes a double-ended needle having a first end extending distally from the body and a second end extending into the cavity for penetrating a seal on a cartridge received in the cavity.

The proximal end of the body may include an opening for directing a cartridge axially therethrough into the cavity. A plunger assembly may then be provided on the proximal end of the body for engaging a piston in the cartridge received in the cavity for delivering a medication in the cartridge through the needle. The plunger assembly may include a plug that is attachable to the proximal end of the body for encapsulating the cartridge in the cavity, and a plunger slidably attached to the plug.

In a preferred embodiment, the detent is molded on the shield and the detent pocket is molded into the body. The detent is preferably deflectable radially outward for withdrawing the detent from the detent pocket to allow retraction of the shield. For example, a lever may be molded on the shield having the detent on a first end thereof, the lever being pivotable for deflecting the detent radially outward.

In first embodiment, the latch may be a hinged member on a second end of the lever opposite the detent, the hinged member being receivable in a pocket in the shield for preventing subsequent pivoting of the lever. In a second embodiment, the latch may be a hinged member on the shield, the hinged member engageable with the lever to prevent subsequent pivoting of the lever. In a third embodiment, the latch may be a hinged member on a second end of the lever opposite the detent, the hinged member being engageable to the first end of the lever for preventing subsequent pivoting of the lever.

In another embodiment of the present invention, a syringe is provided that includes a three-position shield. The syringe includes a body having proximal and distal ends and a cavity therein for receiving a medicine cartridge, and a shield that is slidably attached to the body. A needle cannula is provided on the distal end of the body having a proximal portion extending proximally into the cavity, and a distal portion extending distally beyond the distal end of the body. A plunger assembly is provided on the proximal end of the body for distally directing a piston in a cartridge received in the cavity to deliver medication from the cartridge through the needle. Cooperating detents and detent pockets are provided on the body and shield to temporarily hold the shield in a retracted position wherein the distal portion of the needle is exposed, to temporarily hold the shield in an intermediate guarded position wherein the distal portion of the needle is substantially covered, and to substantially permanently lock the shield in a fully extended position distally beyond the intermediate position.

More preferably, the cooperating detent and detent pockets include a set of detents molded on the shield. Proximal, intermediate, and distal sets of detent pockets are molded into the body, the intermediate set of detent pockets having sloping proximal and distal edges for facilitating sliding the detents out of the intermediate set of detent pockets to direct the shield towards one of the retracted and fully extended positions. The distal set of detent pockets preferably have substantially blunt proximal edges for preventing proximal movement of the shield once the set of detents are received in the distal set of detent pockets.

In accordance with another aspect of the present invention, a method is provided for injecting a medication into a patient using a syringe having a slidable shield thereon in a retracted position wherein a needle of the syringe is exposed. Medication is injected from the syringe into a patient through the needle. The shield is then advanced axially until cooperating detents on the syringe engage to secure the shield in an extended position that substantially covers the needle.

If desired, the cooperating detents may be disengaged to allow retraction of the shield to expose the needle before engaging the latch. Additional medication may be injected from the syringe into the patient through the needle, and then the shield may be advanced again to the extended position. When it is desired to dispose of the syringe, a latch may be engaged to substantially permanently lock the cooperating detents in engagement, thereby substantially permanently locking the shield in the extended position.

In a preferred embodiment, the syringe includes a body and a shield having the cooperating detents thereon, as described above. When it is desired to disengage the cooperating detents, a deflectable portion of the shield may be directed radially outward to disengage detents on the deflectable portion from cooperating detents on the body. More preferably, the deflectable portion is a lever molded to the shield, which may be engaged with the latch to prevent subsequent deflection of the lever. With the shield substantially permanently locked in the extended position, covering the contaminated needle, the syringe may then be disposed of. Thus, a syringe in accordance with the present invention may substantially reduce the risk of accidental needle sticks during use and disposal of the syringe.

Other objects and features of the present invention will become apparent from consideration of the following description taken in conjunction with the accompanying drawings.

BRIEF DESCRIPTION OF THE DRAWINGS

FIGS. 2A and 2B are side views of a body for the aspirating syringe of FIG. 1.

FIGS. 7A and 7B are side views of a plunger for the aspirating syringe of FIG. 1.

FIG. 8 is a side view of an alternative embodiment of a plunger for the aspirating syringe of FIG. 1.

FIG. 9 is a side view of a second preferred embodiment of a shield for the aspirating syringe of FIG. 1.

FIGS. 10A and 10B are details of a latch and lever on the shield of FIG. 9, with the latch disengaged from and engaged with the lever, respectively.

FIGS. 11A and 11B are side views of a third preferred embodiment of a shield for the aspirating syringe of FIG. 1.

FIGS. 12A and 12B are details of a lever and hinged latch on the shield of FIGS. 11A and 11B, with the latch engaged from and engaged with the lever, respectively.

DETAILED DESCRIPTION OF THE PREFERRED EMBODIMENTS

Figure 1A:
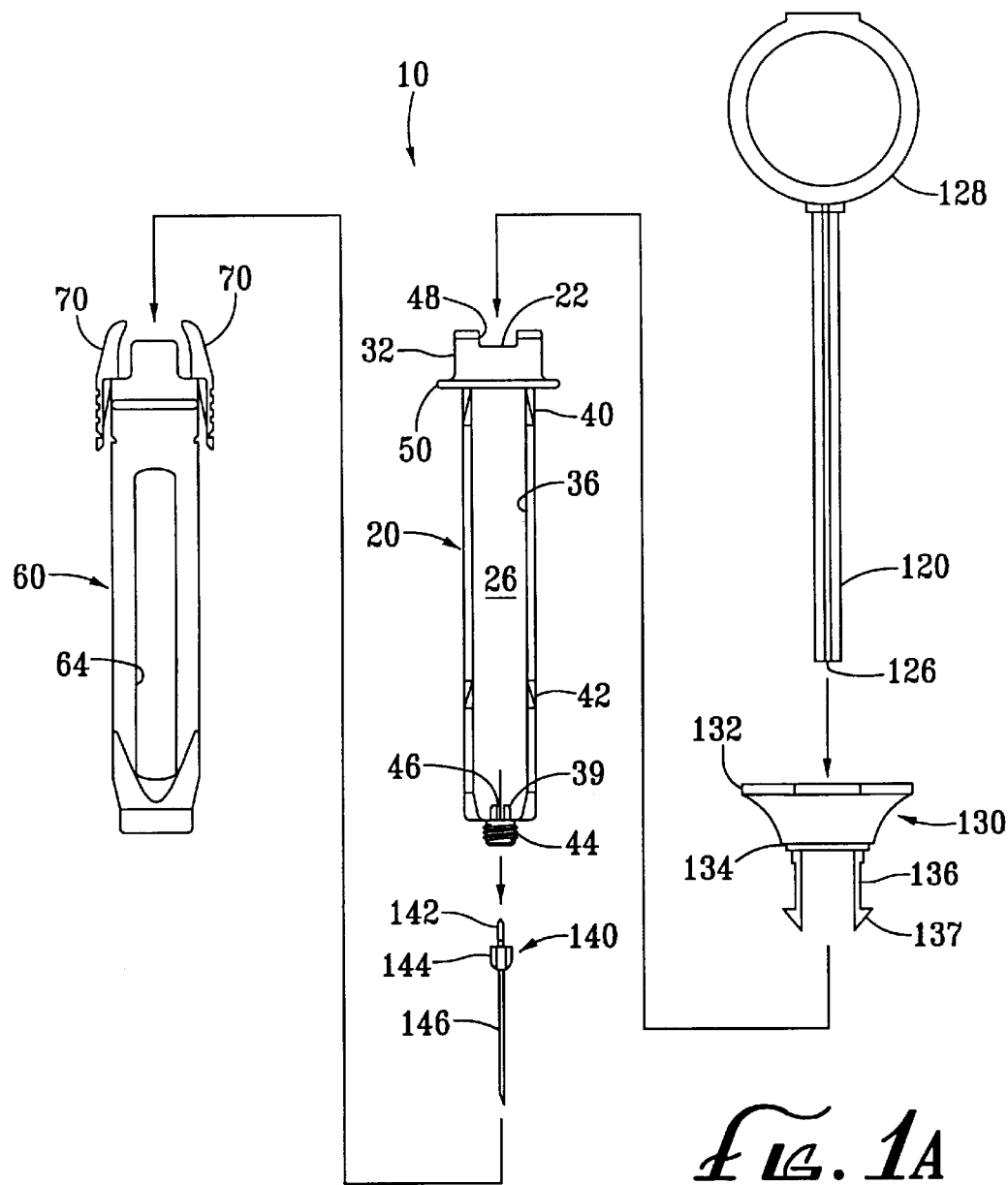
FIG. 1A is an exploded side view of an aspirating syringe with needle shield, in accordance with the present invention.

Turning now to the drawings, FIG. 1A shows a preferred embodiment of an aspirating syringe 10 for holding a medical cartridge or ampoule 90 (shown in FIG. 1B), in accordance with the present invention. Generally, the syringe 10 includes a housing or body 20 for receiving the cartridge 90, a protective case or shield 60 slidably attached to the body 20, a plunger 122, a finger grip plug 130, and a double-ended needle cannula 140. The double-ended needle cannula 140 may be supplied separately, e.g., by the end-user.

The parts are preferably molded from plastic, such as butadiene styrene (commonly know as "k-resin" with styrene added) or polycarbonate, having a clear, colorless finish. Alternatively, a translucent or opaque finish may be provided, possibly including a color, such as latex or flesh tone. In addition, a perfume, scent, or other agent may be added to the plastic before the parts are molded, for example, to associate a desired scent or flavor with the syringe. Thus, during use, the patient may be exposed to a pleasant scent that may offset other odors, such as the odor of the medication or the user's medical gloves, and thereby facilitate the patient being more comfortable and/or relaxed.

Turning to FIGS. 2A–2D, the body 20 has opposing side rails 28 defining two elongate openings or windows 36 extending at least partially between a proximal end 22 and a distal end 24 of the body 20. The side rails 28 have concave inner surfaces 30 defining a cavity 26 in the body 20 for holding a cartridge (not shown). Alternatively, the side rails 28 may include longitudinal ribs (not shown) within the cavity for supporting a cartridge received therein. The outer surfaces of the side rails 28 define a substantially rectangular cross-section for the body 20, providing a substantially rigid structure for protecting the cartridge encapsulated within the body 20.

A collar 32 is molded to the proximal end 22 and has an opening 34 therethrough that communicates with the cavity 26 for inserting a cartridge into the body 20. The collar 32 includes notches 48 that are aligned preferably with tapered grooves 49 (in phantom) extending along an inside surface of the collar 32 between the notches 48 and the windows 36. The notches 48 preferably provide easy orientation for facilitating attachment of the finger grip plug 130, as described further below. The collar 32 also includes a finger grip ring 50 which extends radially out from the collar 32, allowing the body 20 to be held more easily.

A threaded hub 44 extends from the distal end 24 of the body 20 that has an opening 46 extending axially therethrough. The double-ended needle cannula 140 (see FIG. 1A) may be attached to the hub 44 by directing a proximal portion 142 of the cannula 140 through the opening 46 into the cavity 26 until an internally threaded hub 144 on the cannula 140 engages the hub 44 on the body 20. The cannula 140 may then be threaded onto the hub 44 such that a distal portion 146 of the cannula 140 extends distally from the body 20 for injection into a patient. Alternatively, a needle cannula may be integrally molded into the distal end 24 of the body 20 such that a proximal portion extends into the cavity 26 and a distal portion extends distally beyond the distal end 24 (not shown). In a further alternative, the body 20 may be provided without the hub 44, but with the opening 46, to accommodate a cartridge received in the body 20 that has its own needle (not shown).

In a preferred embodiment, an annular extension or hub 39 is molded within the distal end 24 that extends a short distance into the cavity 26. The hub 39 may engage a resiliently flexible penetrable seal of a cartridge received in the cavity to provide a self-aspirating feature that may be useful, for example, for dental syringes. Additional information on an internal hub for providing a self-aspirating syringe may be found in U.S. Pat. No. 3,583,399 issued to Ritsky, the disclosure of which is expressly incorporated herein by reference. Alternatively, other self-aspirating structures may be provided, such as those disclosed in U.S. Pat. Nos. 4,333,457 and 4,381,779 issued to Marguiles, and U.S. Pat. No. 4,333,456 issued to Webb, the disclosures of which are expressly incorporated herein by reference. In a further alternative, the hub 39 may be eliminated and the syringe 10 aspirated manually by directing the piston distally and then partially proximally, as is described below.

The body 20 also includes one or more radially disposed stop tabs 38 molded onto the body 20, preferably on two opposite sides of the distal end 24, and preferably between the window 36 and the distal end 24 of the body 20. The body 20 also includes a set of proximal detent pockets 40, for example, adjacent to the finger grip ring 50, and a set of distal detent pockets 42 at a more distal location on the body 20. In a preferred embodiment, the proximal detent pockets 40 have sloping distal edges 40a to facilitate shield advancement, and the distal detent pockets 40 have substantially blunt proximal edges 42b to prevent shield retraction, as described further below.

Turning to FIGS. 3A–4B, the protective case or shield 60 is a tubular member adapted to be slidably attached to the body 20. The shield 60 includes four side walls 61a, 61b, an open proximal end 62, and an open distal end 63. Assembly tabs 72 with tapered interior surfaces 73 are molded into and extend proximally from side walls 61a. Finger flanges 76 are also molded onto and extend radially from the side walls 61a. The two opposite walls 61a each include elongate windows 64 that facilitate observation of a cartridge received in the body 20, and that also provide traveling slots for the stop tabs 38 on the body 20. The windows 64 and the stop tabs 38 together limit the relative movement of the body 20 and the shield 60, as described further below. In an alternative embodiment, a cross-member (not shown) may be provided that extends across the window 64 to further limit the travel of the stop tab 38, such as that shown in co-pending U.S. application Ser. No. 08/814,199 filed Mar. 10, 1997, the disclosure of which is incorporated herein by reference.

Figure 4A:
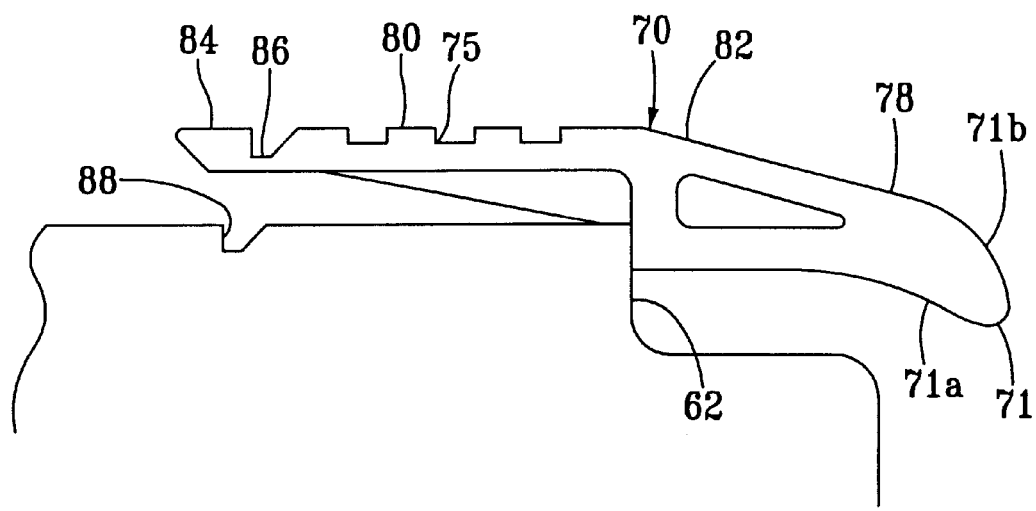
FIGS. 4A and 4B are details of a pivotable lever on the shield of FIGS. 3A and 3B with a locking latch thereon disengaged from and engaged with a pocket in the shield, respectively.
Figure 4B:
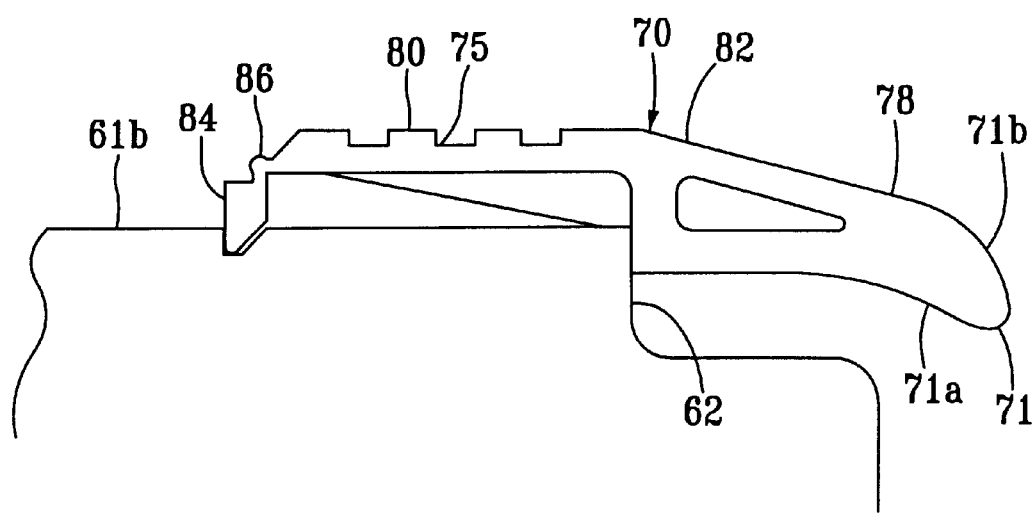

A pair of levers 70 are preferably molded on or otherwise attached to the proximal end 62 of the shield 60. Each lever 70 includes a proximal portion 78 and a distal portion 80 that are pivotable about an intermediate portion 82. An outer surface 75 of the lever 70 may include transverse grooves or other raised or recessed elements to facilitate manipulation thereof. A pair of detents 71 extend from the proximal portion 78, while a hinged latch 84 extends from the distal portion 80. The detents 71 preferably have sloping distal edges 71a and substantially blunt proximal edges 71b. As best seen in FIGS. 4A and 4B, the latch 84 includes a hinged region 86 that facilitates engagement of the latch 84 in a pocket 88 in the side wall 61b.

The distal portion 80 of the lever 70 may be directed radially inward, i.e., towards side wall 61b, for example, by squeezing the distal portions 80 of the opposing levers 70 towards one another, to deflect the detents 71 radially outward. Once the latch 84 is bent and received in the pocket 88, however, the distal portion 80 may no longer be directed radially inward, thereby substantially preventing subsequent deflection of the detents 71, as described further below.

Figure 5A:
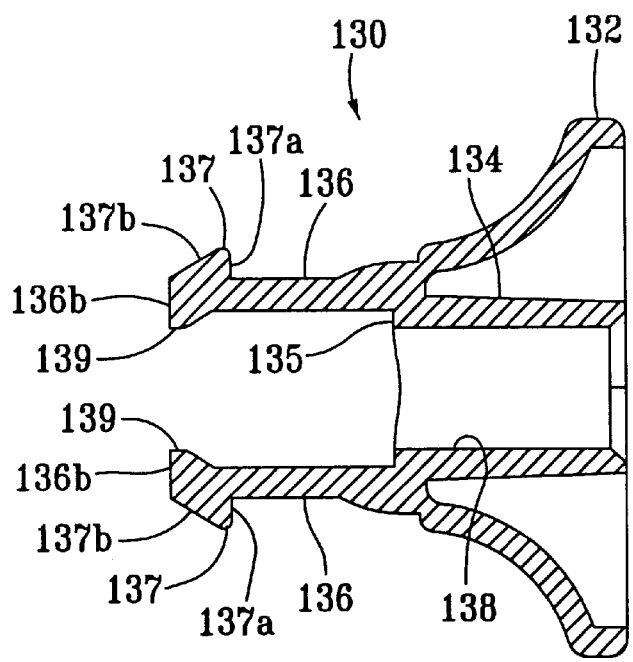
FIGS. 5A and 5B are cross-sectional side and end views, respectively, of a finger grip plug for the aspirating syringe of FIG. 1.
Figure 5B:
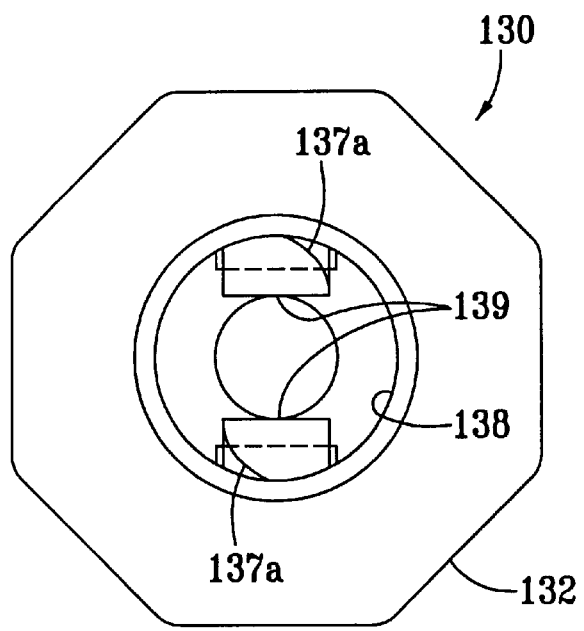

Referring now to FIGS. 5A and 5B, the finger grip plug 130 includes a central hub 134, a finger flange 132 extending radially from the hub 134, and a pair of fingers 136 extending distally from the hub 134. The hub 134 also has a passage 138 extending axially therethrough for receiving the plunger 120 (see FIGS. 6A and 6B). The fingers 136 have outwardly disposed locking tabs or detents 137 molded thereto that include rounded leading edges 137a and substantially blunt trailing edges 137b for facilitating attachment and detachment of the plug 130 from the body 20, as described further below. The fingers 136 also include inwardly disposed ledges 139 that partially obstruct the passage 138 for preventing removal of the piston 94 from the cartridge 90 after use, also as described further below.

Turning to FIGS. 7A and 7B, the plunger 120 includes a shaft 122, preferably having a cruciform cross-section. A thumb ring 128 is molded on a proximal end 124 of the shaft 122, although alternative proximal ends may be provided, such as a "T" type finger flange (not shown). A resiliently deflectable tab 129 is molded to the shaft 122 adjacent a recessed region 125 such that it extends proximally and radially outward from the distal end 126.

Figure 6A:
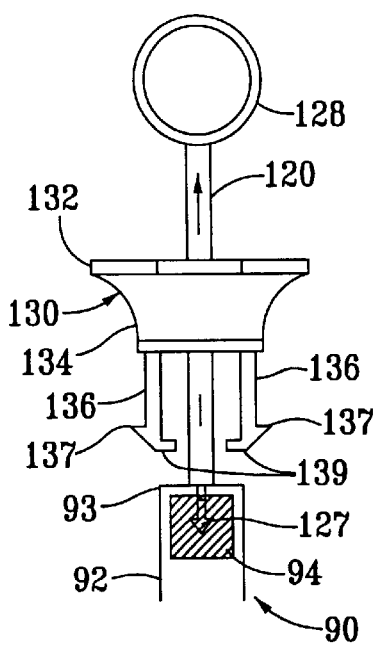
FIGS. 6A and 6B are side views showing locking fingers of a finger grip plug engaging a piston of a cartridge to prevent its withdrawal from the cartridge.
Figure 6B:
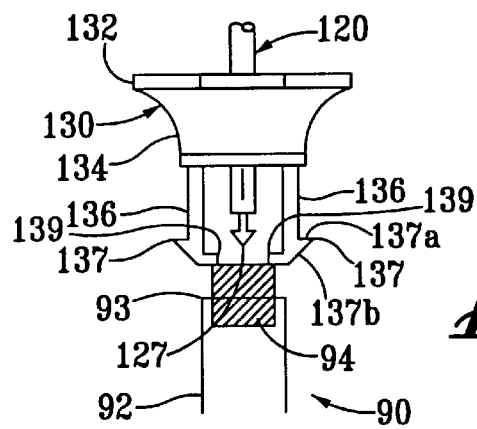

A harpoon 127 is molded or otherwise attached to a distal end 126 of the shaft 122 that facilitates securely engaging the piston 94 of the cartridge 90 to control movement of the piston 94 distally and proximally using the plunger 120 (see FIGS. 6A and 6B). Additional information on the harpoon 127 may found in U.S. Pat. No. 5,437,647 issued to Firth et al., the disclosure of which is expressly incorporated herein by reference.

Alternatively, as shown in FIG. 8, the distal end 126' of the shaft 122 may be provided with a substantially blunt distal surface 127' for allowing distal movement of the piston 94 without directly engaging it. In further alternatives, other distal ends may be provided, such as a threaded nipple or bore for engaging a mating bore or nipple on a piston, an adhesive material, and the like, if appropriate for attaching to or otherwise directing the piston of a desired medical cartridge.

Prior to use, the syringe 10 is generally provided with the body 20 and shield 60 pre-assembled and the plunger 120 and finger grip plug 130 pre-assembled. To pre-assemble the body 20 and shield 60, the distal end 24 of the body 20 is inserted into the proximal end 62 of the shield 60, with the windows 36 in the body 20 aligned with the side walls 61a of the shield 60 having the windows 64 therein. Each stop tab 38 preferably includes a sloped or ramped distal edge 38a that engages the tapered interior edge 73 of the respective assembly tabs 72, allowing the stop tab 38 to pass under the side wall 61a until the stop tab 38 enters the respective window 64.

If a cross-member (not shown) is provided across one or more of the windows 64, the ramped distal edge 38a may also allow the stop tab 38 to pass under the cross-member until it enters and travels freely in a desired portion of the respective window 64. The detents 71 are directed radially outward to prevent them from engaging the distal detent pockets 42, e.g., by squeezing the distal portions 80 of the levers 70, and then the shield 60 is directed proximally until the detents 71 enter and engage the proximal detent pockets 40, holding the shield 60 in a retracted or unguarded position.

A conventional removable needle cap (not shown) may be placed over the distal portion 146 of the needle 140 and attached to the hub 44 prior to retraction of the shield 60. Alternatively, the detents 71 may be permitted to engage the distal detent pockets 42, thereby providing a storage position for the shield 60 in which the needle 140 is covered.

The plunger 120 and finger grip plug 130 are pre-assembled by inserting the distal end 126 of the plunger 120 into the passage 138 in the plug 130. As the plunger 120 is advanced distally, the tab 129 enters the passage 138 and is deflected radially inward, until it exits the passage 138, whereupon it resiliently returns to its radially outward position. The plunger 120 may be directed distally and proximally, but its proximal movement is limited when the tab 129 abuts a distal edge 135 of the hub 134. Thus, the tab 129 slidably secures the plunger 120 to the plug 130, preventing the plunger 122 from being completely removed from the plug 130.

Figure 1B:
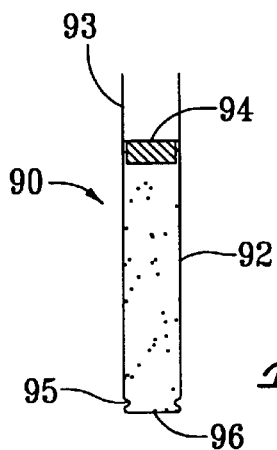
FIG. 1B is a side view of a cartridge that may be received in a body of the syringe of FIG. 1A.
Figure 2C:
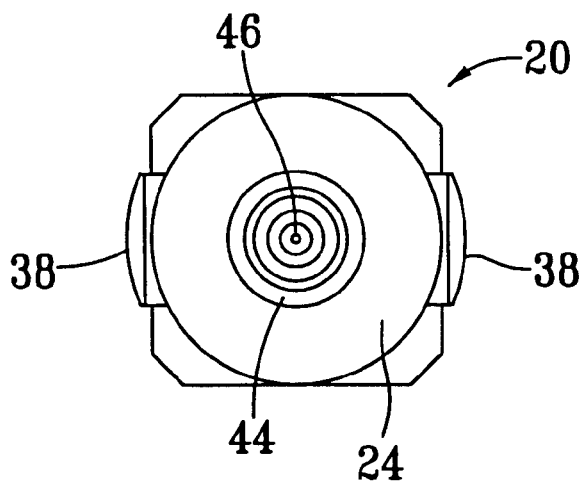
FIGS. 2C and 2D are distal and proximal end views, respectively, of the body of FIGS. 2A and 2B.
Figure 2D:
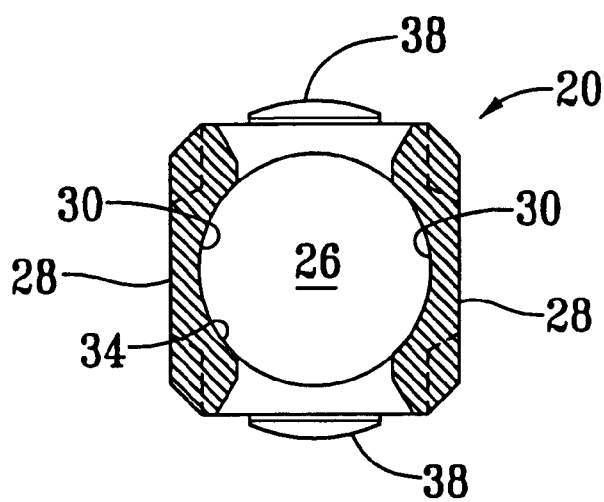
Figure 3A:
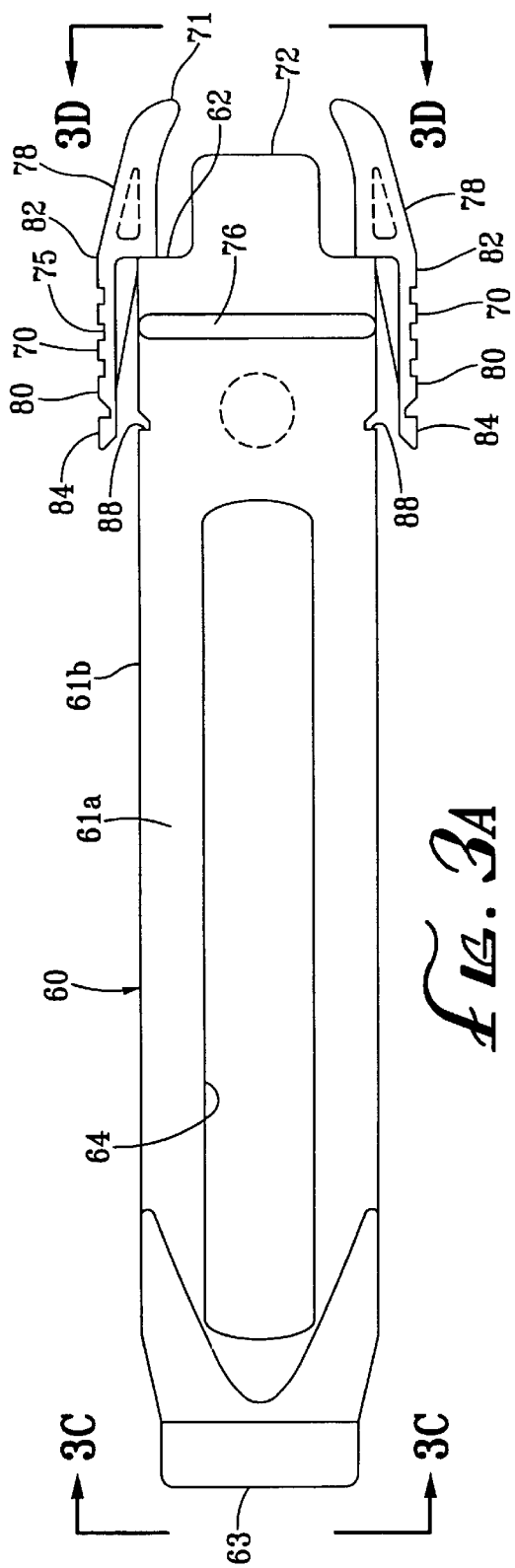
FIGS. 3A and 3B are side views of a first preferred embodiment of a shield for the aspirating syringe of FIG. 1.
Figure 3B:
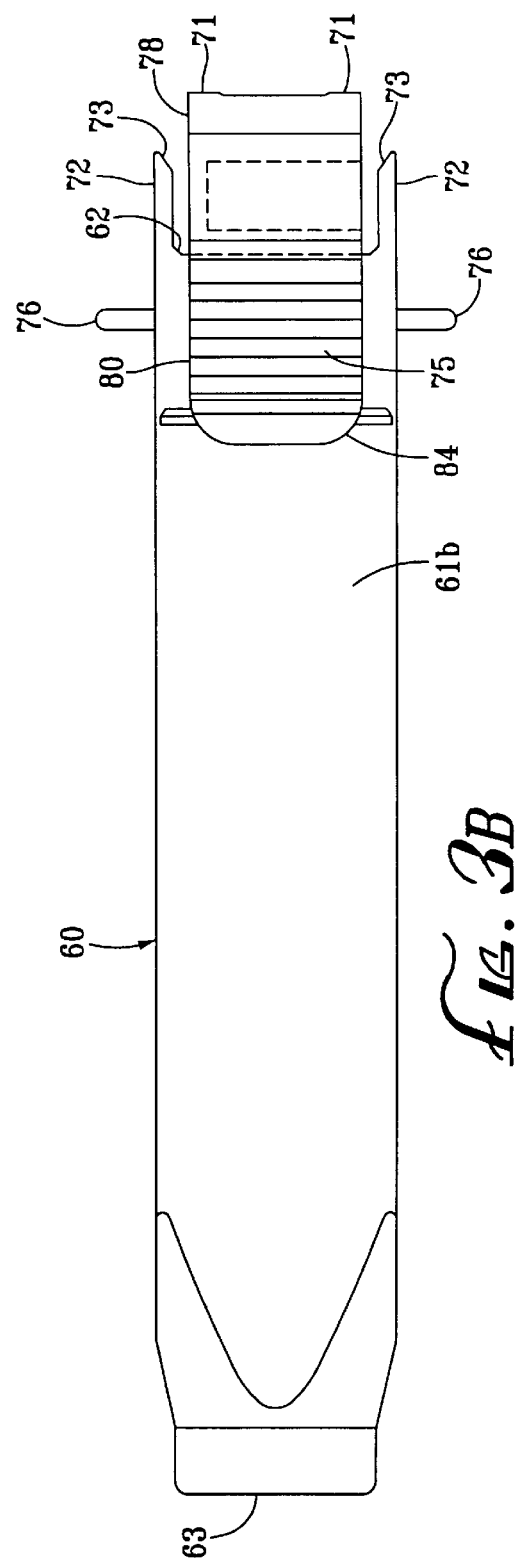
Figure 3C:
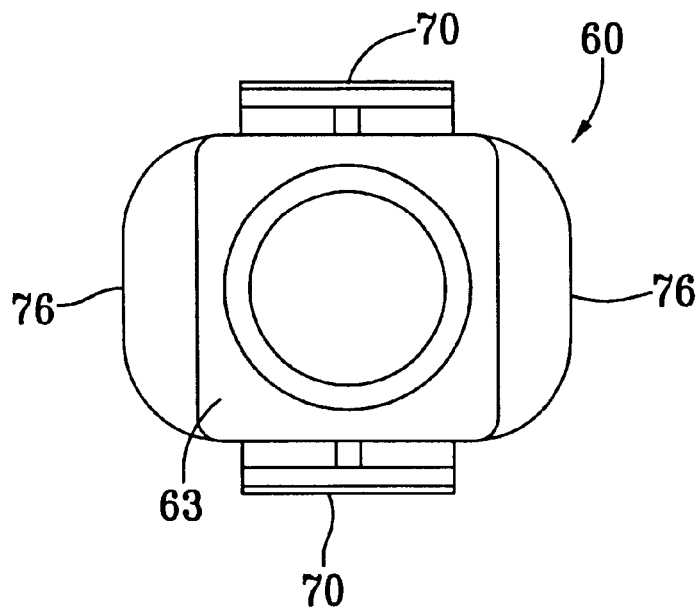
FIGS. 3C and 3D are proximal and distal end views, respectively, of the shield of FIGS. 3A and 3B.
Figure 3D:
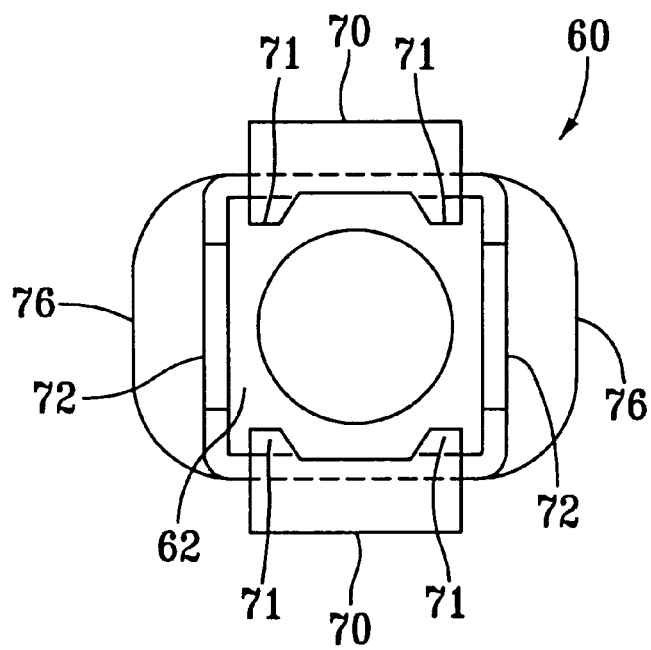

The pre-assembled body 20 and shield 60, and plunger 120 and plug 130 are then ready to receive a cartridge 90, such as a conventional unit dose ampoule, as shown in FIG. 1B. The cartridge 90 generally includes a barrel 92, a distal end 95 including a penetrable seal 96, and a proximal end 93 having a piston 94 therein. The cartridge 90 is generally pre-filled with medicine, such as an anaesthetic, vaccine or other therapeutic or diagnostic agent.

The distal end 94 of the cartridge 90 is inserted into the open proximal end 22 of the body 20 and directed distally. The finger grip plug 130 is attached to the proximal end 22 of the body 20, for example, by aligning the fingers 136 on the plug 130 with the notches 48 in the collar 32 on the body 20, and directing the plug 130 distally. As tapered edges 137b of the detents 137 engage the notches 48, the fingers 136 are deflected radially inward, enter the tapered pockets 49, and pass through the collar 32. Upon reaching the windows 36, the fingers 136 resiliently expand radially outward again. The locking detents 137 have substantially blunt proximal edges 137a, which engage the distal side of the finger grip ring 50, thereby substantially securing the plunger 120 and plug 130 to the body 20, and encapsulating the cartridge 90 within the cavity 26.

As the plug 130 is attached to the body 20, the distal ends 136b of the fingers 136 preferably engage the proximal end 93 of the cartridge 90, forcing the cartridge 90 forward until the penetrable seal 96 is penetrated by the proximal portion 142 of the needle cannula 140 and/or the distal end 95 of the cartridge 90 abuts the distal end 24 of the body 20. Thus, the fingers 136 prevent substantial subsequent proximal movement of the cartridge 90. Alternatively, the cartridge 90 may be manually directed completely into the cavity 26 of the body 20, e.g., until the seal 96 is penetrated by the needle cannula 140, before attaching the plug 130.

The plunger 120 is attached to the piston 94, for example, by holding the syringe 10 and pushing down on the thumb ring 128, e.g., against the user's palm, thereby forcing the harpoon 127 into the piston 94, as may be seen in FIG. 6A. The plunger 120 may then be used to direct the piston distally and/or proximally within the cartridge 90.

With the shield 60 in the retracted position, the distal portion 146 of the needle cannula 140 extends through the open distal end 63 of the shield 60 and is exposed for injection into a patient. Thus, the syringe 10 is ready to be used to deliver the medicine contained within the cartridge 90 in a conventional manner. During injection, the windows 64 and 36 facilitate observation of the barrel 92 of the syringe 90, allowing the user to monitor delivery of the medicine.

In addition, the syringe 10 may facilitate aspirating the cartridge 90 during an injection, as is often done for dental applications. In the preferred embodiment, which includes aspirating hub 39, the plunger 120 may be directed distally a relatively short distance, thereby injecting a small amount of medication, such as a dental anaesthetic, into the patient. The distal force applied to the cartridge 90 via the plunger 120 causes the seal 96 on the cartridge 90 to be deflected around the hub 39 until the distal end 95 of the cartridge 90 abuts the distal end 24 of the body 20.

The plunger 120 may then be released, whereupon the resiliency of the seal 96 pulls the cartridge 90 proximally to relieve the stress thereon, thereby creating a small vacuum within the cartridge 90. If the needle cannula 140 is in communication with a blood vessel, a small amount of blood may be pulled into the cartridge 90 by this vacuum, notifying the user to remove the needle 140 and inject at another site. In this embodiment, it is preferred that the plunger 120' of FIG. 8 be used that does not include a harpoon, although the plunger 120 of FIGS. 7A and 7B may also be used.

Alternatively, if the aspirating hub 39 is not provided (not shown), the plunger 120 of FIGS. 7A and 7B is preferably used, as it allows the user to directly pull the plunger 120 proximally to manually aspirate the syringe 10. For this alternative embodiment, the fingers 136 on the plug 130 preferably include the inwardly disposed ledges 139 when it is desired to reuse the syringe 10, as is explained further below.

After the medication is dispensed, the needle 95 is withdrawn from the patient, and the self-shielding feature of the syringe 10 may be activated. With the fingers of one hand, the body 20 may be held while the shield 60 is slid distally into the extended position, covering the needle 95. As the shield 60 is advanced distally, the sloping distal edges 71a of the detents 71 slide along the sloping distal edges 40a of the proximal detent pockets 40 detents 71, deflecting the detents 71 radially outward until they leave the proximal detent pockets 40. When the shield 60 reaches the extended position, the detents 71 become aligned with the distal detent pockets 42 and resiliently snap into the distal detent pockets 42. In the extended position, the substantially blunt proximal edges 71b of the detents 71 may engage the substantially blunt proximal edges 42b of the distal detent pockets 42, thereby preventing subsequent proximal movement and locking the shield 60 in the extended position. Substantially simultaneously, the stop tabs 38 on the body 20 reach the distal end of the windows 64, thereby preventing the shield 60 from being directed further distally, i.e., thereby substantially retaining the shield 60 on the body 20 at the extended position.

If the syringe 10 is to be disposed of, the latches 84 on the levers 70 may be bent until they are received in the pockets 88 in the shield 60. This prevents the levers 70 from being subsequently pivoted, and thereby substantially permanently locks the detents 71 in the distal detent pockets 42, and consequently locks the shield 60 in the extended position.

For some applications, however, it may be desirable to use the syringe 10 for one or more additional injections. For example, with a dental syringe, a dentist may use a single cartridge to deliver a series of anaesthetic injections into a single patient before disposing of the syringe. In such cases, after a first injection and advancement of the shield 60 to the extended position, the user may retract the shield 60 simply by squeezing both of the levers 70, thereby deflecting the detents 71 outwardly and disengaging them from the distal detent pockets 42, and then retracting the shield 60. When the shield 60 reaches the retracted position, the levers 70 may be released, causing the detents 71 to be received again in the proximal detent pockets 40. Alternatively, the body 20 may include a deflectable portion (not shown) for disengaging the detents 71 from the distal detent pockets 42.

After the second injection, the shield 60 may be advanced again to the extended position, as described above. This procedure may be repeated as many times as desired, until the syringe 10 is to be finally disposed of. At the time of disposal, the latches 84 may be bent until they are received in the pockets 88, as described above.

Figure 5C:
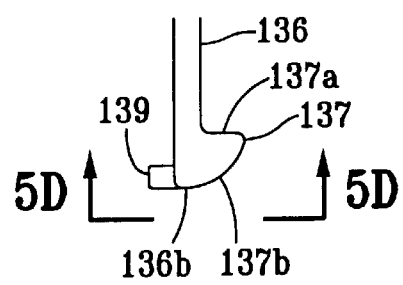
FIGS. 5C and 5D are details of a locking finger and detent on the plug of FIGS. 5A and 5B for securing the plug to the body.
Figure 5D:
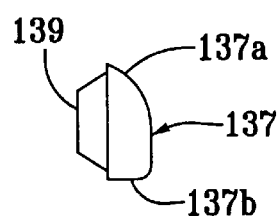

Prior to disposal, it may be desirable to recycle one or more of the parts of the syringe 10 for subsequent sterilization and reuse. For example, it may be desirable to recover the plunger 120 and plug 130, as they may be removed from the syringe 10 without risking exposure of the contaminated needle 140. As best seen in FIGS. 5C and 5D, in the preferred embodiment shown, the leading edges 137a of the detents 137 on the plug 130 are rounded such that the plug 130 may be twisted about the longitudinal axis of the syringe 10 to disconnect the plug 130 from the body 20. As the plug 130 is turned, the leading edges 137a engage the side rails 28 of the body 20, thereby deflecting the fingers 136 radially inward and allowing the plug 130 to be directed proximally through the collar 32 and removed from the body 20. Alternatively, if it is desired to substantially permanently attach the plug 130 to the body 20, the leading edges 137a may be substantially blunt (not shown), similar to the trailing edges 137b.

As the plug 130 and plunger 120 are removed from the body 20, the plunger 120 may pull the piston 94 proximally within the cartridge 90, for example, if the plunger 120 has a harpoon 127 that is engaging the piston 94, risking removing the piston 94 and releasing medicine from the cartridge 90. To substantially reduce the risk of this occurring, the plunger 120 preferably includes a recessed region 125 on the distal end 126 of the shaft 122, and the plug 130 includes inwardly disposed ledges 139 on the fingers 136. The cross-section of the shaft 122 of the plunger 120 may prevent the fingers 136 of the plug 130 from being deflected inward if an attempt is made to twist the plug 130. To allow twisting, the plunger 120 may be withdrawn proximally until the recessed region 125 is aligned with the fingers 136. As this occurs, the piston 94 may also be pulled proximally, but once the piston 94 abuts the inwardly disposed ledges 139 of the plug 130, the harpoon 127 may be disengaged from the piston 94. The recessed region 125 may then provide sufficient space around the plunger 120, thereby allowing the plug 130 to be twisted. As it is twisted, the fingers 136 may deflect inward, thereby allowing the plug 130 to be disengaged from the body 20. The plug 130 and plunger 120 may then be recycled, while the body 20 and shield 60, with the cartridge 90 therein, disposed of in a conventional manner.

In an alternative embodiment, it may desirable to provide a side-loading syringe (not shown), rather than an axial loading syringe 10, as described above. For example, on one side of the syringe 10, the windows 36, 64 may be sufficiently wide to allow a cartridge to be inserted into the cavity 26 through them. The window 36 in the body 20 may include tabs or rails (not shown) that may deflect to facilitate insertion, yet resiliently return to engage the cartridge 90 to prevent subsequent removal from the cavity 26. In such an alternative embodiment, the plug 130 may be molded directly to the proximal end 22 of the body (not shown), or may be attachable, as described above. Otherwise, a side loading syringe may operate substantially the same as the axial loading syringe 10 described above.

Turning to FIGS. 9, 10A and 10B, a second preferred embodiment of a shield 160 is shown that may be incorporated into a syringe including a body, plug, and plunger substantially as described above (not shown). The shield 160 includes four side walls 161a, 161b defining proximal and distal ends 162, 163, and having assembly tabs 172, finger flanges 176, and pivotable levers 170 molded on the proximal end 162, similar to those described above. The levers 170 include a proximal portion 178 having detents 171 thereon, an intermediate portion 182 extending from the side wall 161b, and a distal portion 180 having a hook 184 thereon.

A hinged latch 186 having a catch 188 on its end extends substantially transversely from the side wall 161b adjacent the hook 184. As best seen in FIG. 10B, the latch 186 may be bent until the hook 184 on the lever 170 is received in the catch 188, thereby substantially permanently locking the lever 170 from being pivoted and preventing subsequent deflection of the detents 171 radially outwardly. Alternative cooperating connectors may be provided on the latch 186 and the distal portion 180 of the lever 170, as will be appreciated by those skilled in the art. Otherwise, the operation of the shield 160 is similar to the shield 60 described above. The shield 160 may be advanced from a retracted position to an extended position on a body (not shown). The levers 170 may be squeezed to release the detents 171 from distal detent pockets (not shown) on the body and allow retraction of the shield 160, or the latches 186 may be engaged with the levers 170 to substantially permanently lock the shield 160 in the extended position.

Turning to FIGS. 11A–12B, a third preferred embodiment of a shield 260 is shown that includes four side walls 261a, 261b defining proximal and distal ends 262, 263, and having assembly tabs 272, finger flanges 276, and pivotable levers 270 molded on the proximal end 262, similar to those described above. The levers 270 include a proximal portion 278 having detents 271 thereon, an intermediate portion 282 extending from the side wall 261b, and a distal portion 280 connected to the intermediate portion 282 by a hinge 281.

The proximal and distal portions of the levers 270 include cooperating balls and sockets 284, 286, or other cooperating connectors (not shown).

Use of the shield 260 is similar to the shields described above. When it is desired to lock the shield 260, however, the distal portions 280 of the levers 270 are pivoted about their hinges 281 until the balls 284 are received in the corresponding sockets 286, thereby preventing return of the distal portions 280 to their distal position. Without the lever arms provided by the distal portions, 280, the levers 270 may no longer be pivotable, thereby preventing subsequent radially outward deflection of the detents 271 and substantially permanently locking the shield 260 in its extended position.

Figure 13:
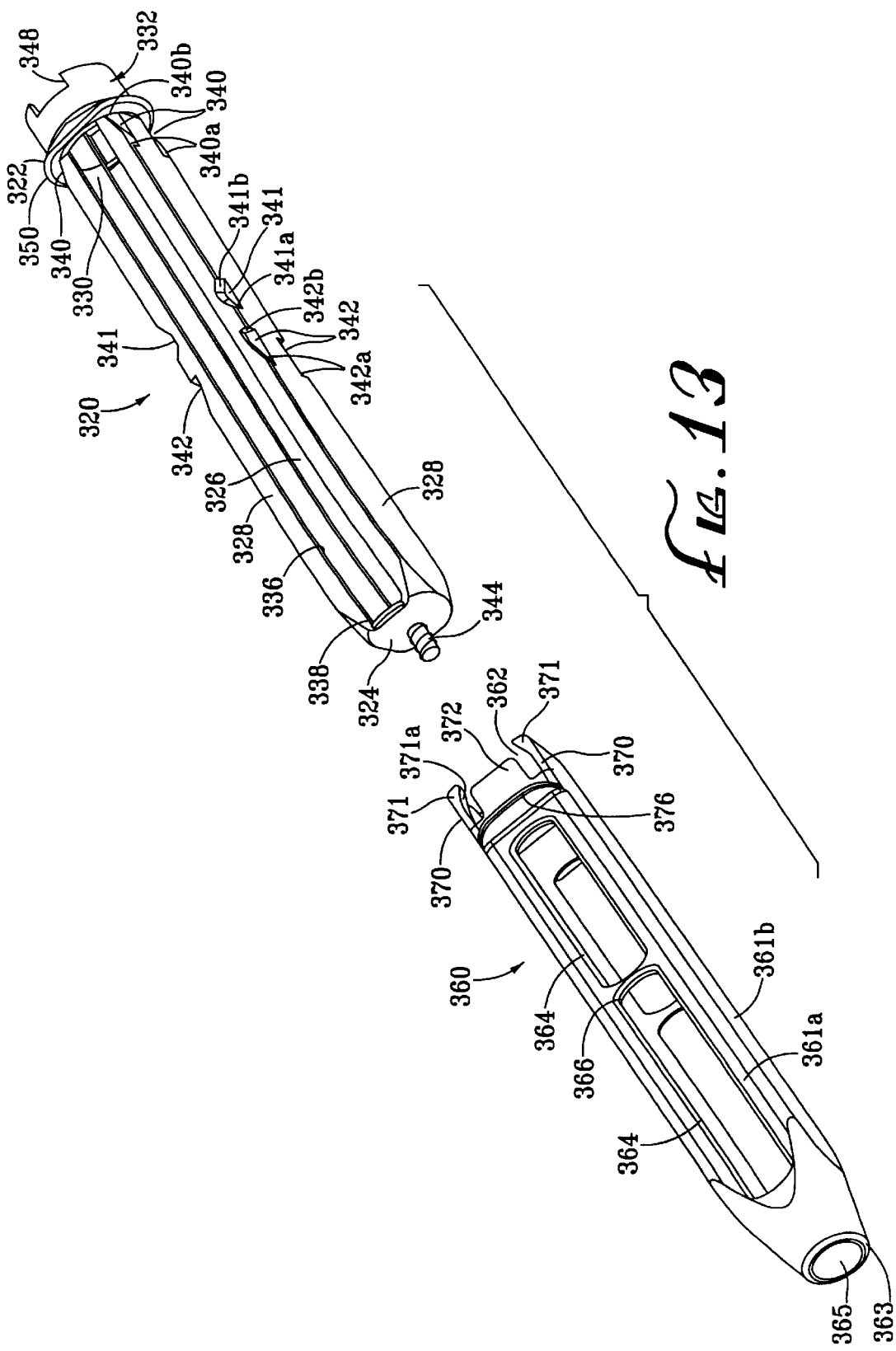
FIG. 13 is an exploded perspective view of another preferred embodiment of a body and shield for a syringe, in accordance with the present invention.

Turning to FIG. 13, another preferred embodiment of a body 320 and shield 360 is shown. The body 320 includes opposing side rails 328 defining proximal and distal ends 322, 324 and windows 336. A collar 332 is molded on the proximal end 362, and stop tabs 338 and a threaded hub 344 are molded on the distal end 363, similar to the embodiments described above. In addition, the body 320 includes proximal and distal detent pockets 340, 342 having sloping distal edges 340a, 342a, and substantially blunt proximal edges 340b, 342b, also similar to the previously described embodiments. Unlike the previous embodiments, however, the body 20 also includes intermediate detent pockets 341 having sloping distal and proximal edges 341a, 341b located between the proximal and distal detent pockets 340, 342.

The shield 360 includes four side walls 361a, 361b defining a proximal end 362 having assembly tabs 372 and finger flanges 376 thereon, and a distal end 363 having an opening 365 therethrough. Windows 364 are provided in opposing side walls 361a that include cross-members 366 that limit travel of the stop tabs 338 on the body 320, as described above. The proximal end 363 also includes a pair of resiliently deflectable fingers 370 having inwardly oriented detents 371 thereon.

The body 320 and shield 360 may be pre-assembled, a cartridge (not shown) inserted into the cavity 326, and a plug and plunger assembly (not shown) attached to the collar 332, similar to the embodiments described above. The shield 360 is preferably initially provided in a retracted position, wherein the detents 371 engage the proximal detent pockets 340, thereby exposing a needle and needle cap (not shown) attached to the hub 344 on the distal end 324 of the body 320. The needle cap may be removed and an injection made, as described above.

After an injection is made, the shield 360 may be advanced until the detents 371 are received in the intermediate detent pockets 341. In this intermediate position, the shield 360 substantially covers the needle extending from the body 320, thereby protecting a user from accidental needle sticks. If a second or subsequent injection is desired, the shield 360 may be retracted back to the retracted position. The sloping proximal edges 341b of the intermediate detent pockets 341 allow the detents 371 to slide and deflect radially outwardly until they leave the intermediate detent pockets 341 and the shield 360 may be directed proximally until the detents 371 again enter the proximal detent pockets 340.

If no further injections are desired, the shield 360 may be advanced until the detents 371 are received in the distal detent pockets 342. The sloping distal edges 341a of the intermediate detent pockets 341 allow the detents 371 to slide and deflect radially outwardly. Once the detents 371 are received in the distal detent pockets 342, the substantially blunt proximal edges 371b, 342b of the detents 371 and distal detent pockets 342 prevent the shield 360 from being retracted from this fully extended position. Thus, the shield 360 may be substantially permanently locked in the fully extended position to facilitate safe disposal of the syringe.

In alternative embodiments, the body 320 and shield 360 may include other detent arrangements (not shown) that cooperate to temporarily hold the shield 360 in the retracted position, or the intermediate guarded position, and that substantially permanently lock the shield 360 in the fully extended position covering the needle to facilitate disposal. The detent arrangement corresponding to the intermediate position should allow axial displacement of the shield 360 by application of a manual force, but provide sufficient axial resistance to substantially prevent accidental movement of the shield 360 from the intermediate position, i.e., preventing exposure of the needle or accidental locking of the shield 360 in the fully extended position until desired.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

What is claimed is:

1. A self-shielding syringe, comprising:
   a body having proximal and distal ends and a cavity therein for receiving a medicine cartridge, the distal end having an opening through which a needle may extend;
   a shield slidably attached to the body and slidable between a retracted position wherein a needle extending from the distal end of the body is exposed through a distal end of the shield, and an extended position wherein the needle is substantially covered by the shield;
   a cooperating detent and detent pocket on the shield and body for releasably holding the shield in the extended position; and
   a latch for locking the detent in the detent pocket for preventing subsequent retraction of the shield from the extended position.

2. The syringe of claim 1, wherein the shield comprises a deflectable portion that is deflectable radially outwardly for disengaging the detent from the detent pocket to allow retraction of the shield.

3. The syringe of claim 2, wherein the deflectable portion comprises a lever on the shield having one of the detent and detent pocket on a first end thereof, the lever being pivotable for directing the one of the detent and detent pocket radially outwardly to disengage the detent from the detent pocket.

4. The syringe of claim 3, wherein the latch comprises a hinged member on a second end of the lever opposite the detent, the hinged member being receivable in a pocket in the shield for preventing subsequent pivoting of the lever.

5. The syringe of claim 3, wherein the latch comprises a hinged member on the shield, the hinged member engageable with the lever to prevent subsequent pivoting of the lever.

6. The syringe of claim 3, wherein the latch comprises a hinged member on a second end of the lever opposite the detent, the hinged member being engageable to the first end of the lever for preventing subsequent pivoting of the lever.

7. The syringe of claim 1, further comprising a needle extending from the distal end of the body.

8. The syringe of claim 7, wherein the needle is molded directly into the distal end of the body.

9. The syringe of claim 7, wherein the needle and the distal end of the body comprise cooperating threaded hubs for attaching the needle onto the body.

10. The syringe of claim 7, wherein the needle comprises a double-ended needle having a first end extending distally from the body and a second end extending into the cavity for penetrating a seal on a cartridge received in the cavity.

11. The syringe of claim 1, further comprising a cooperating detent and detent pocket on the shield and body for releasably holding the shield in the retracted position.

12. The syringe of claim 1, wherein the body comprises an aspirating hub extending from the distal end of the body into the cavity for engaging a resilient seal on the cartridge received in the cavity.

13. The syringe of claim 1, wherein the proximal end of the body comprises an opening for directing a cartridge axially therethrough into the cavity.

14. The syringe of claim 1, further comprising a plunger assembly on the proximal end of the body for engaging a piston in the cartridge received in the cavity for delivering a medication in the cartridge through the needle.

15. The syringe of claim 14, wherein the plunger assembly comprises a plug attachable to the proximal end of the body for engaging a cartridge received within the cavity.

16. A self-shielding syringe, comprising:
a body having proximal and distal ends and a cavity therein for receiving a medical cartridge, the distal end having an opening through which a needle may extend;
a shield slidably attached to the body and slidable between a retracted position wherein a needle extending from the distal end of the body is exposed through a distal end of the shield, and an extended position wherein a needle is substantially covered by the shield;
a cooperating detent and detent pocket on the shield and body for holding the shield in the extended position, the shield having a deflectable portion for selectively disengaging the detent from the detent pocket to allow retraction of the shield from the extended position; and
a latch on the shield for lockably preventing deflection of the deflectable portion to prevent subsequent disengagement of the detent from the detent pocket, thereby substantially permanently locking the shield in the extended position.

17. The syringe of claim 16, wherein the deflectable portion comprises a lever on the shield, the lever being pivotable on the shield for directing the detent radially outward to disengage the detent from the detent pocket.

18. The syringe of claim 17, wherein the latch comprises a hinged member that is bendable between the lever and the shield for preventing subsequent pivoting of the lever when the latch is engaged.

19. The syringe of claim 18, wherein the hinged member is molded to the lever and is bendably receivable in a pocket in the shield.

20. The syringe of claim 16, further comprising a needle extending from the distal end of the body.

21. The syringe of claim 16, further comprising a cooperating detent and detent pocket on the shield and body for releasably holding the shield in the retracted position.

22. The syringe of claim 16, further comprising a plunger assembly on the proximal end of the body for engaging a piston in the cartridge received in the cavity for delivering a medication in the cartridge through the needle.

23. The syringe of claim 22, wherein the plunger assembly comprises a plug attachable to the proximal end of the body for engaging a cartridge received within the cavity.

24. A self-shielding dental syringe, comprising:
a body having proximal and distal ends and a cavity therein for receiving a medical cartridge;
a needle cannula on the distal end of the body having a proximal portion extending proximally into the cavity, and a distal portion extending distally beyond the distal end of the body;
a plunger assembly substantially permanently attached to the proximal end of the body for distally directing a piston in a cartridge received in the cavity to deliver medication from the cartridge through the needle;
a shield slidably attached to the body;
cooperating detents and detent pockets on the body and shield to temporarily hold the shield in a retracted position wherein the distal portion of the needle is exposed, to temporarily hold the shield in an intermediate guarded position wherein the distal portion of the needle is substantially covered, and to substantially permanently lock the shield in a fully extended position distally beyond the intermediate position.

25. The syringe of claim 24, wherein the cooperating detents and detent pockets comprise:
a set of detents on the shield; and
proximal, intermediate, and distal sets of detent pockets on the body, the intermediate set of detent pockets having sloping proximal and distal edges for facilitating sliding the detents out of the intermediate set of detent pockets to direct the shield towards one of the retracted and fully extended positions.

26. The syringe of claim 25, wherein the distal set of detent pockets have substantially blunt proximal edges for preventing proximal movement of the shield once the set of detents are received in the distal set of detent pockets.

27. A method for injecting a medication into a patient using a syringe having a slidable shield thereon in a retracted position wherein a needle of the syringe is exposed, the method comprising:
injecting medication from the syringe into a patient through the needle;
advancing the shield axially until cooperating detents on the syringe engage to secure the shield in an extended position that substantially covers the needle; and
engaging a latch to substantially permanently lock the cooperating detents in engagement, thereby substantially permanently locking the shield in the extended position.

28. The method of claim 27, comprising the additional steps of:
disengaging the cooperating detents to allow retraction of the shield to expose the needle before engaging the latch;
injecting additional medication from the syringe into the patient through the needle; and
advancing the shield to the extended position.

29. The method of claim 28, wherein the syringe comprises a body and a shield having the cooperating detents thereon, and wherein the step of disengaging the cooperating detents comprises deflecting a deflectable portion of the shield outward to disengage detents on the deflectable portion from cooperating detents on the body.

30. The method of claim 29, wherein the deflectable portion comprises a lever.

31. The method of claim 30, wherein the step of engaging a latch comprises engaging the lever with the latch to prevent subsequent deflection of the lever.

32. The method of claim 29, wherein the syringe further comprises a plunger assembly including a plunger slidably attached to a plug, and wherein the method further comprises the steps of:
inserting a medicine cartridge into the body through an axial opening in the body until an interior of the cartridge communicates with the needle; and attaching the plug of the plunger assembly to the body, thereby encapsulating the cartridge therein.

33. The method of claim 32, wherein the step of injecting medicine comprises engaging a piston in the cartridge with the plunger on the plunger assembly, thereby forcing medicine in the interior of the cartridge through the needle.

* * * * *